(12) United States Patent
Mihara et al.

(10) Patent No.: US 10,989,686 B2
(45) Date of Patent: Apr. 27, 2021

(54) GAS SENSOR

(71) Applicant: NGK Spark Plug Co., LTD., Nagoya (JP)

(72) Inventors: Shunya Mihara, Nagoya (JP); Takehiro Oba, Nagoya (JP)

(73) Assignee: NGK Spark Plug Co., LTD., Nagoya (JP)

( * ) Notice: Subject to any disclaimer, the term of this patent is extended or adjusted under 35 U.S.C. 154(b) by 139 days.

(21) Appl. No.: 16/353,330

(22) Filed: Mar. 14, 2019

(65) Prior Publication Data

US 2019/0285578 A1 Sep. 19, 2019

(30) Foreign Application Priority Data

Mar. 15, 2018 (JP) .............................. JP2018-047685

(51) Int. Cl.
*G01N 27/406* (2006.01)
*G01N 27/416* (2006.01)
*G01N 33/00* (2006.01)
*G01N 27/407* (2006.01)

(52) U.S. Cl.
CPC ..... *G01N 27/4162* (2013.01); *G01N 27/4062* (2013.01); *G01N 27/4077* (2013.01); *G01N 33/0037* (2013.01)

(58) Field of Classification Search
CPC ................................................. G01N 27/4062
See application file for complete search history.

(56) References Cited

U.S. PATENT DOCUMENTS 9,151,728 B2 * 10/2015 Kato .................. G01N 27/4062
2017/0370877 A1 12/2017 Mihara et al.

FOREIGN PATENT DOCUMENTS

JP 2017-227524 A 2/2017

* cited by examiner

*Primary Examiner* — Alexander S Noguerola
(74) *Attorney, Agent, or Firm* — Leason Ellis LLP (57) ABSTRACT

A gas sensor includes a sensor element, metal terminals, a tubular separator holding the metal terminals, lead wires connected to rear ends of the metal terminals, and an elastic member that holds the lead wires extending rearward from the separator. Each metal terminal includes a forward end portion electrically connected to an electrode portion, a central portion, and a lead wire connection portion. The forward end portion or the central portion is held by the separator. The central portion and the lead wire connection portion are connected to each other through a neck portion. The rearward-facing rearmost surface of the central portion is engaged with a forward-facing surface of the separator, and the circumferential length of a first connection portion between the central portion and the neck portion is longer than the circumferential length of a second connection portion between the lead wire connection portion and the neck portion.

4 Claims, 12 Drawing Sheets

GAS SENSOR

This application claims the benefit of Japanese Patent Application No. 2018-047685, filed Mar. 15, 2018, which is incorporated herein by reference in its entirety.

FIELD OF THE INVENTION

The present invention relates to a gas sensor including a sensor element for detecting the concentration of a subject gas.

BACKGROUND OF THE INVENTION

One known gas sensor for detecting the concentration of oxygen or NOx in exhaust gas from an automobile etc. includes a sensor element that uses a solid electrolyte.

In such a gas sensor, to output the output of the sensor element that corresponds to the concentration of the subject gas to the outside, metal terminals are brought into contact with electrode portions (electrode pads) disposed in a rear end portion of the sensor element so as to electrically connect the metal terminals to the electrode portions, and lead wires are connected to crimp portions at rear ends of the metal terminals by crimping the crimp portions. The metal terminals are held in a separator formed of an insulating member, and the lead wires extend from the rear end of the separator through a grommet to the outside of the gas sensor.

Figure 12A:
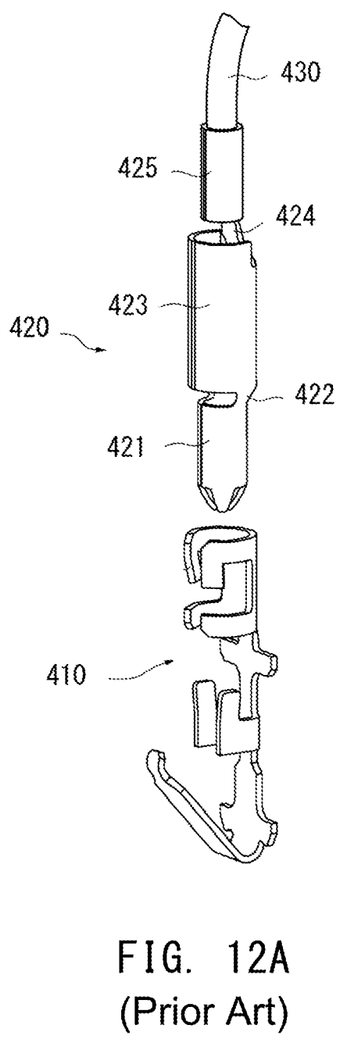
FIGS. 12A and 12B are perspective views showing a conventional two-piece metal terminal.
Figure 12B:
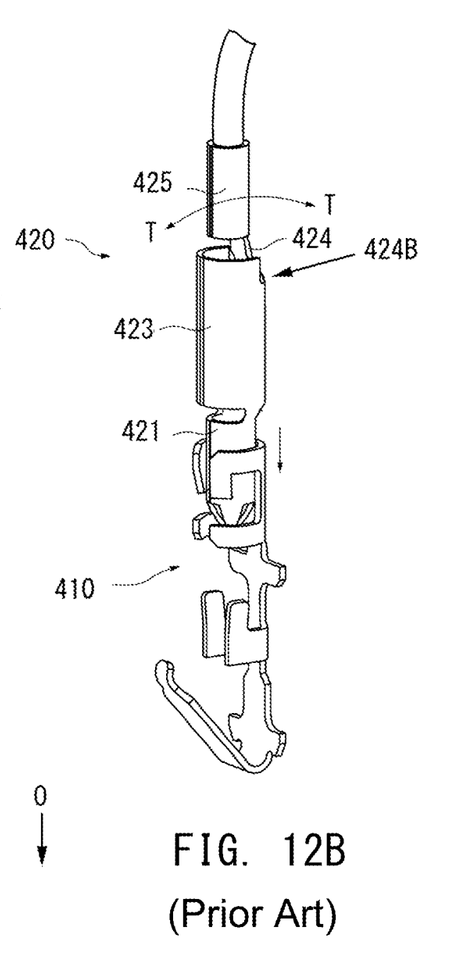

In one previously developed technique shown in FIGS. 12A and 12B, two-piece metal terminals each composed of forward and rear metal terminal members 410 and 420 connected in the direction of an axial line O are used. The rear metal terminal member 420 is crimped and connected to a lead wire 430 and is used as a guide that facilitates insertion of the lead wire 430 into the separator (See FIGS. 4 and 8 of Japanese Unexamined Publication No. 2017-227524).

The rear metal terminal member 420 includes, sequentially from the forward end side, a forward end portion 421 connected to the forward metal terminal member 410, a central portion 423, a lead wire connection portion 425 connected to the lead wire 430. The forward end portion 421 is connected to the lead wire connection portion 425 through the central portion 423. Specifically, the central portion 423 is connected to the forward end portion 421 through a first neck portion 422 and to the lead wire connection portion 425 through a second neck portion 424. The stiffness of the first neck portion 422 is higher than the stiffness of the second neck portion 424. This allows the rear metal terminal member 420 to be reliably connected to the forward metal terminal member 410. Moreover, even when an undue force is applied to the rear metal terminal member 420, the lead wire 430 is prevented from coming off.

In the rear metal terminal member 420, the outer surface of the central portion 423 must be engaged with the wall surface of an insertion hole of the separator, and the lead wire connection portion 425 is reduced in diameter, by means of crimping, for connection with the lead wire 430. Therefore, the lead wire connection portion 425 is smaller in diameter than the central portion 423. In this case, when the central axis of the lead wire connection portion 425 is offset from the central axis of the central portion 423, the rear metal terminal member 420 is anisotropic about its central axis, and therefore its attachment direction must be specified. Moreover, an undue force may be applied to the lead wire connected to the lead wire connection portion within the insertion hole of the separator. Therefore, as shown in FIGS. 12A and 12B, the second neck portion 424 extends toward the rear end side with a radially inward inclination such that the central axis of the lead wire connection portion 425 coincides with the central axis of the central portion 423.

Problems to be Solved by the Invention

However, when the central portion 423 and the lead wire connection portion 425 are connected through the second neck portion 424 having a smaller axial cross sectional area, the lead wire connection portion 425 and the central portion 423 wobble in the radial direction T when the gas sensor vibrates during, for example, travel of the vehicle. It has turned out that, in this case, stress concentrates on a connection portion 424B of the second neck portion 424 that is located near the central portion 423 because of leverage and the connection portion 424B breaks or bends.

In the case where the second neck portion 424 is inclined with respect to the direction of the axial line O, stress is generated in the connection portion 424B due to bending during production. In this case, it has turned out that, when the gas sensor with the metal terminals attached thereto vibrates during, for example, travel of the vehicle, the stressed connection portion 424B may break or bend.

Accordingly, an object of the present invention is to provide a gas sensor in which metal terminals held in a separator are prevented from breaking under vibrations etc.

SUMMARY OF THE INVENTION

Means for Solving the Problems

A gas sensor of the present invention which solves the above-mentioned problem comprises: a sensor element extending in a direction of an axial line of the gas sensor, the sensor element having an electrode portion on a surface of a rear end portion thereof; a metal terminal extending in the direction of the axial line and electrically connected to the electrode portion; a tubular separator that holds the metal terminal and is disposed rearward of the sensor element; a lead wire connected to a rear end portion of the metal terminal and extending rearward from the separator; and an elastic member that holds the lead wire extending rearward from the separator. The metal terminal includes a forward end portion electrically connected to the electrode portion, a central portion, and a lead wire connection portion connected to the lead wire, the forward end portion, the central portion, and the lead wire connection portion being integrally formed and arranged in this order from a forward end side, the forward end portion or the central portion being held by the separator. The central portion and the lead wire connection portion are integrally connected to each other through a neck portion whose cross sectional area orthogonal to the direction of the axial line is smaller than a cross sectional area of the central portion or a cross sectional area of the lead wire connection portion. A rearward-facing rearmost surface of the central portion is engaged with a forward-facing surface of the separator. A circumferential length C1 of a first connection portion provided between the central portion and the neck portion is longer than a circumferential length C2 of a second connection portion provided between the lead wire connection portion and the neck portion.

When the gas sensor vibrates, for example, during travel of the vehicle, the metal terminal is unlikely to wobble in the direction of the axial line because the central portion is engaged with the separator. The lead wire connection portion that is not held by the separator wobbles in the radial direction of the metal terminal, but the forward end portion or the central portion held by the separator wobbles only slightly in the radial direction. The lead wire held in the elastic member wobbles only slightly. Therefore, stress tends to be generated in the neck portion between the lead wire connection portion that wobbles greatly in the radial direction and the central portion close to the lead wire connection portion. In particular, it has turned out that the stress concentrates on the first connection portion near the central portion and the first connection portion tends to break or bend.

In this gas sensor, the circumferential length C1 of the first connection portion is longer than the circumferential length C2 of the second connection portion, and the strength of the first connection portion is thereby improved. Since the first connection portion and the second connection portion share the stress, the breakage of the first connection portion can be prevented.

In the gas sensor of the present invention, preferably, the neck portion inclines inwardly toward a rear end side thereof in a radial direction.

When the neck portion inclines inwardly toward the rear end side thereof in a radial direction, the lead wire connection portion is further spaced apart from the wall surface of the insertion hole of the separator and is therefore unlikely to be held by the separator. Therefore, stress concentrates on the first connection portion side of the neck portion to a greater degree, and the present invention is more effective.

In the gas sensor of the present invention, preferably, the first connection portion is located forward with respect to the rearward-facing rearmost surface; two cutouts are respectively formed between the central portion and opposite ends of the first connection portion in a circumferential direction, the cutouts extending forward from the rearward-facing rearmost surface and reaching a virtual line passing through the opposite ends of the first connection portion; and at least one of the cutouts is formed such that its contour is in contact with the virtual line at a plurality of contact points, including a first contact point P1 that is farthest from the neck portion in the circumferential direction, and with the rearward-facing rearmost surface at a second contact point P2, which is closer to the neck portion than the first contact point P1 in the circumferential direction.

The sum of the circumferential length C1 and the total circumferential length of the rearward-facing rearmost surface of the central portion is approximately the same as the maximum circumferential length of the central portion, and there is a trade-off between C1 and the total circumferential length. Namely, when the circumferential length C1 is increased, the total circumferential length is reduced accordingly, so that the rearward-facing rearmost surface may not be easily engaged with the forward-facing surface of the separator.

Therefore, the cutouts are provided such that the second contact point P2 is closer to the neck portion than the first contact point P1 in the circumferential direction. In this case, even when the circumferential length C1 is increased, the total circumferential length is not reduced because the second contact point P2 is closer to the neck portion than the first contact point P1. Therefore, both C1 and the total circumferential length can be increased, and the metal terminal can be reliably held in the separator.

In the gas sensor of the present invention, preferably, the neck portion has a rib that extends in the direction of the axial line so as to straddle at least the first connection portion.

In this gas sensor, the rib improves the strength of the neck portion, so that the breakage of the metal terminal can be further prevented. Since the rib straddles at least the first connection portion, the strength of the first connection portion on which stress concentrates can be further improved.

In the gas sensor of the present invention, preferably, the rib inwardly recesses in a radial direction of the neck portion.

In this gas sensor, since the rib does not protrude outward from the neck portion, the rib does not interfere with the wall surface of the insertion hole of the separator.

Effects of the Invention

In the gas sensor obtained in the present invention, breakage of the metal terminal held in the separator due to vibration etc. is prevented.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Embodiments of the present invention will be described.

Figure 1:
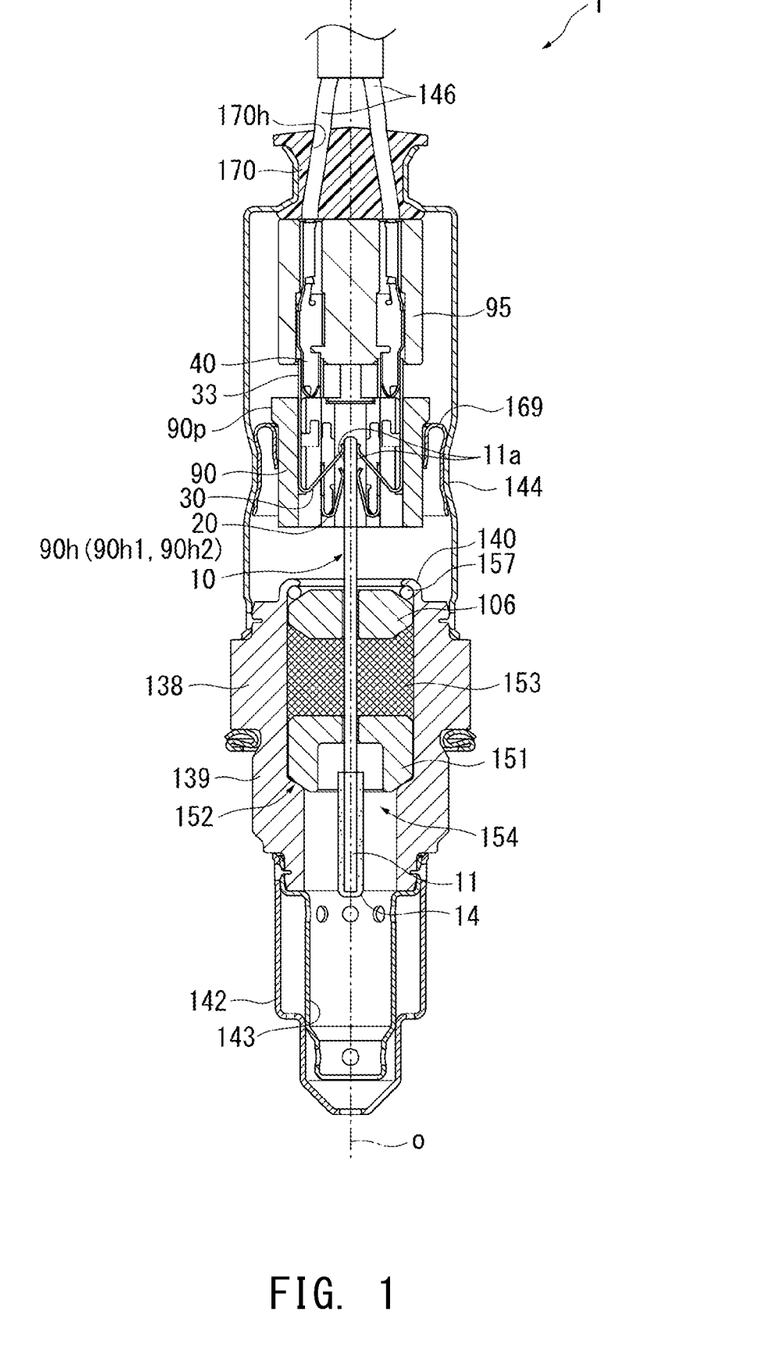
FIG. 1 is a cross-sectional view of a gas sensor according to a first embodiment of the present invention, the cross-sectional view being taken in the direction of an axial line.
Figure 2:
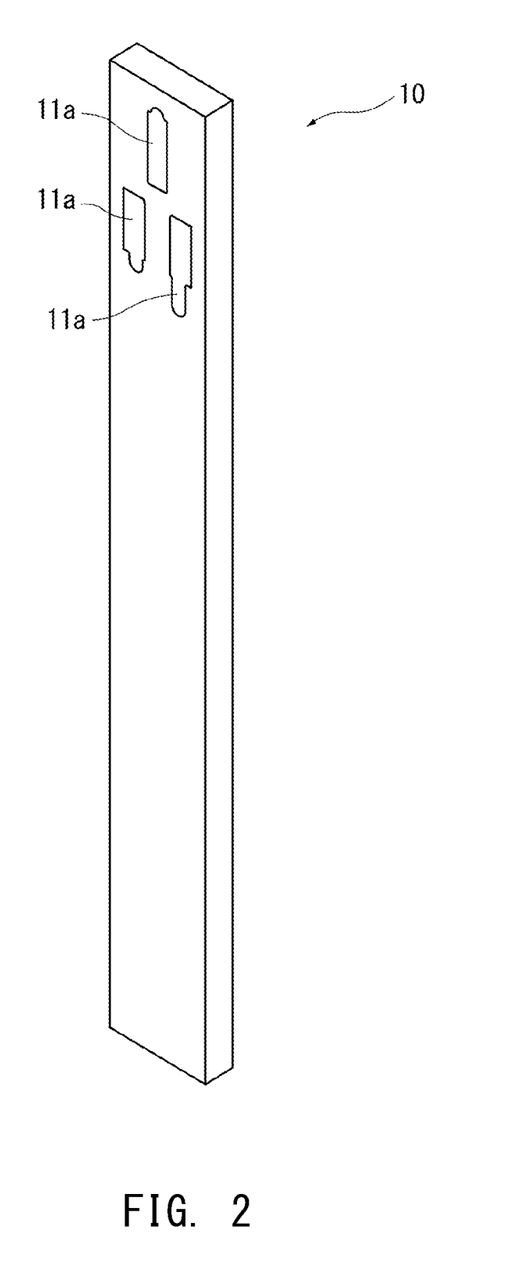
FIG. 2 is a perspective view of a sensor element.
Figure 3A:
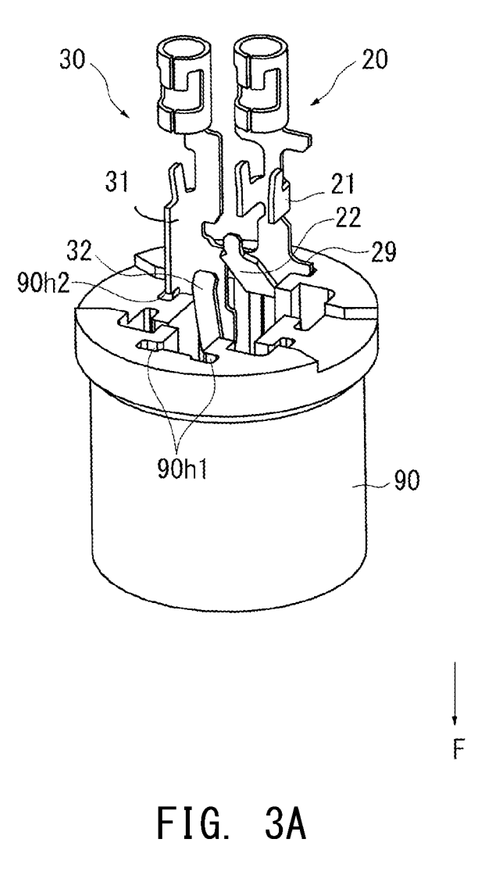
FIGS. 3A and 3B are perspective views showing forward metal terminal members held in a forward separator.
Figure 3B:
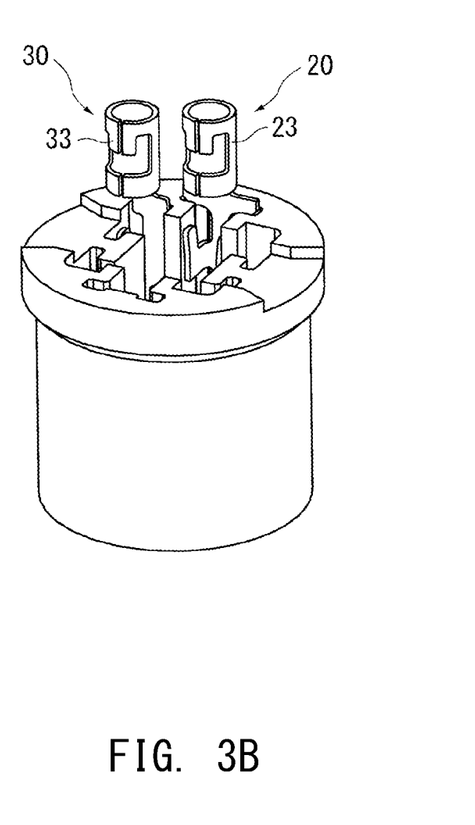
Figure 4:
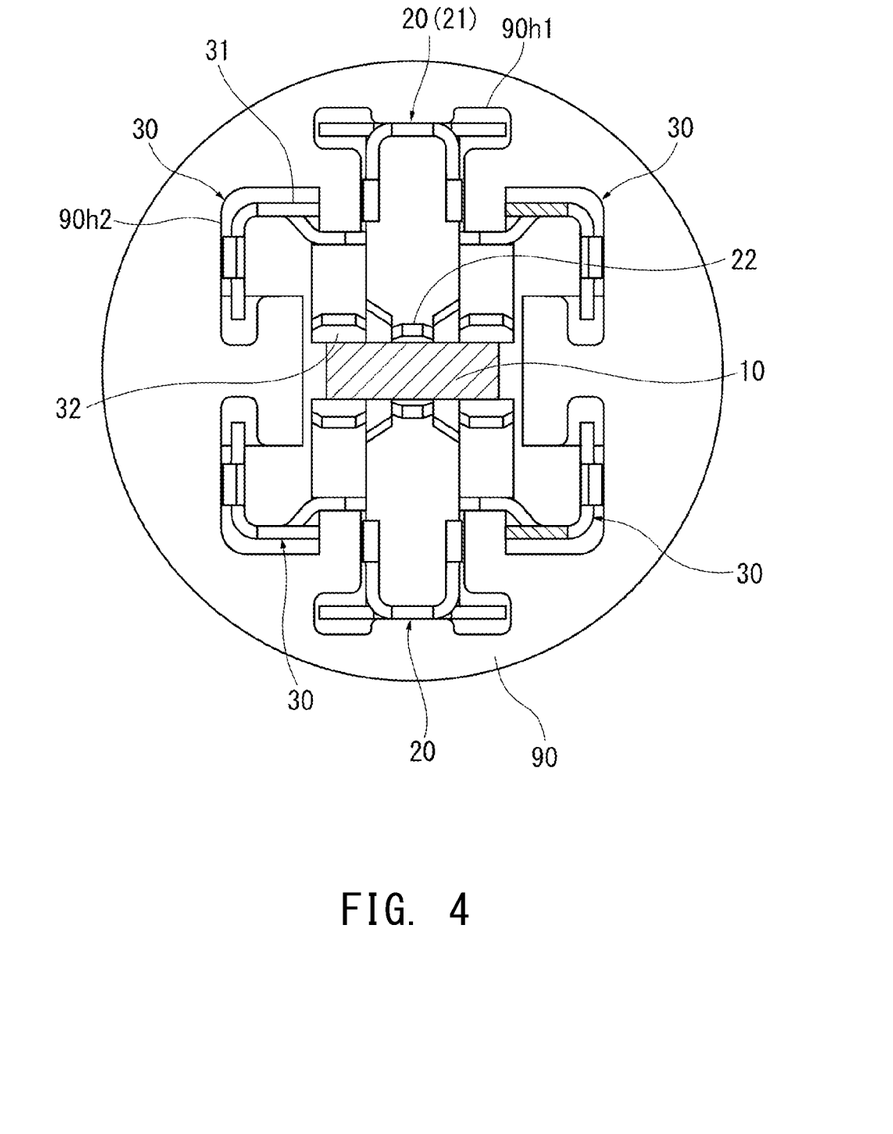
FIG. 4 is a cross-sectional view showing the forward metal terminal members held in the forward separator.
Figure 5:
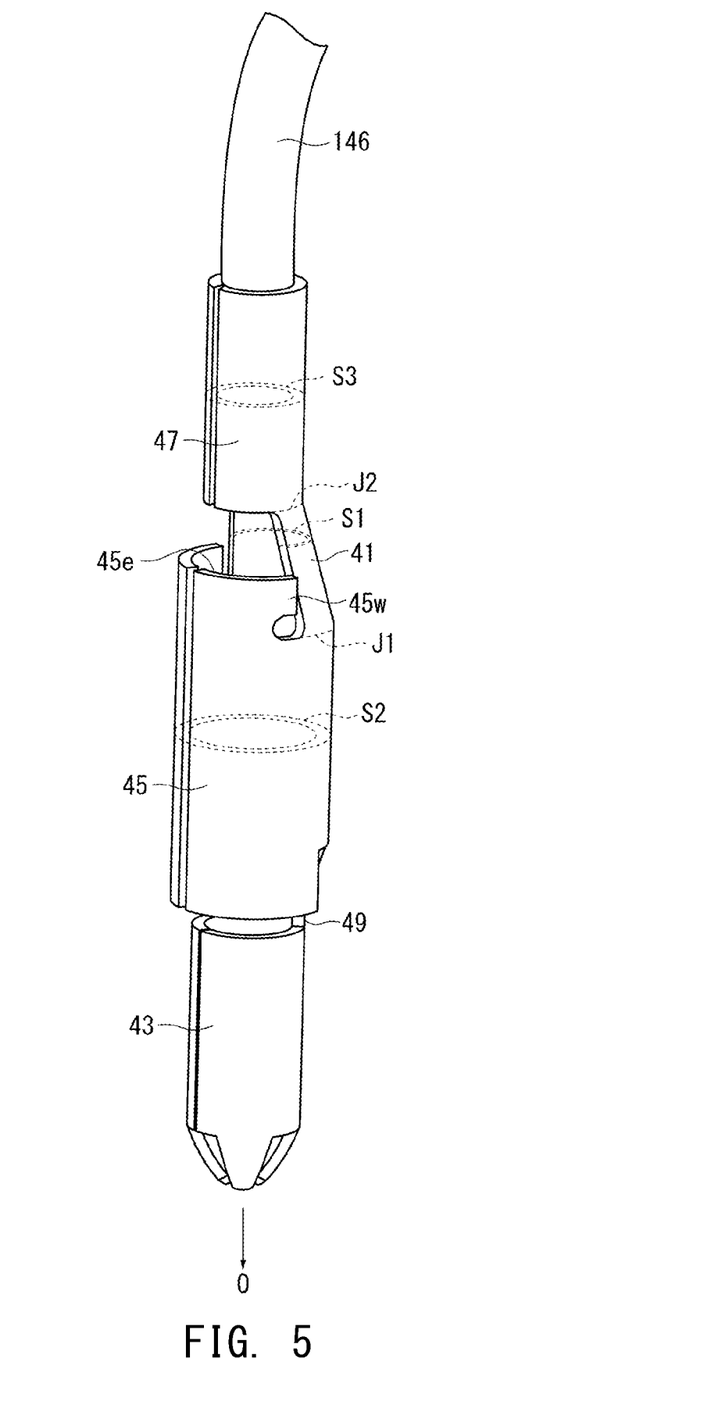
FIG. 5 is a perspective view of a rear metal terminal member.
Figure 6:
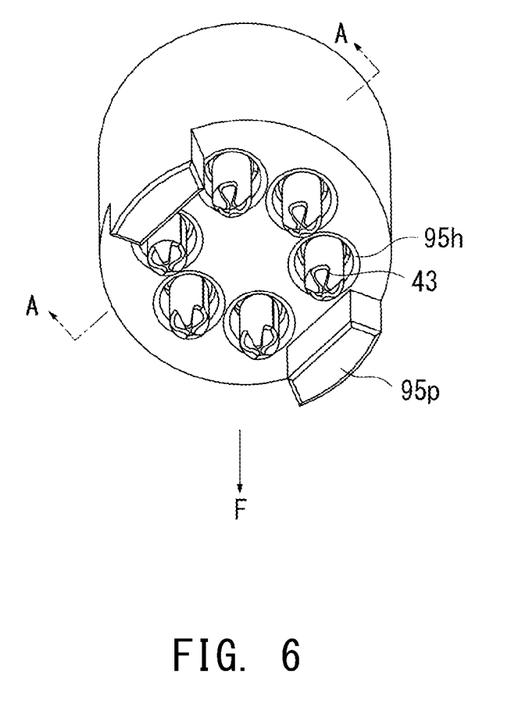
FIG. 6 is a perspective view of rear metal terminal members held in a rear separator.
Figure 7:
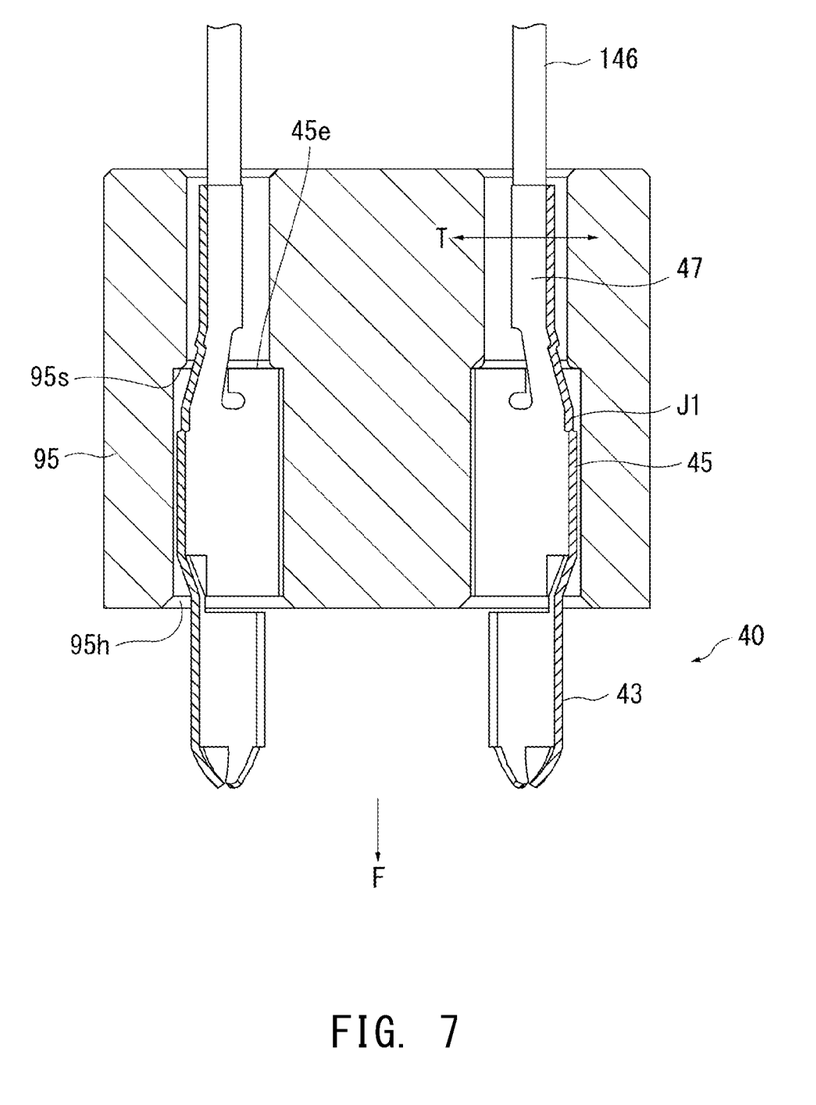
FIG. 7 is a cross-sectional view taken along line A-A in FIG. 6.
Figure 8A:
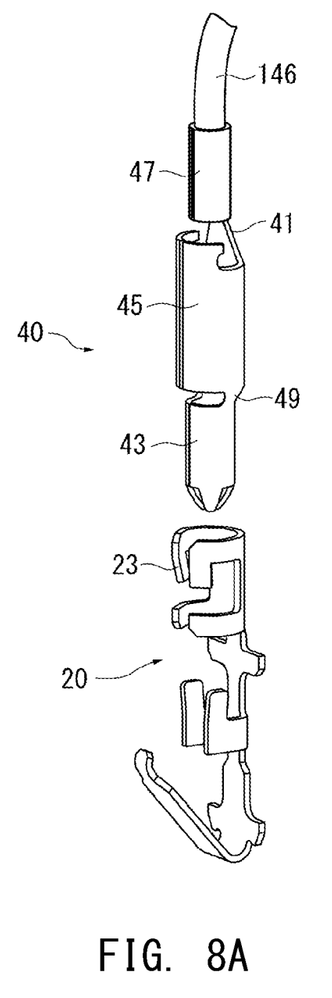
FIGS. 8A and 8B are perspective views showing a rear metal terminal member connected to a forward metal terminal member.
Figure 8B:
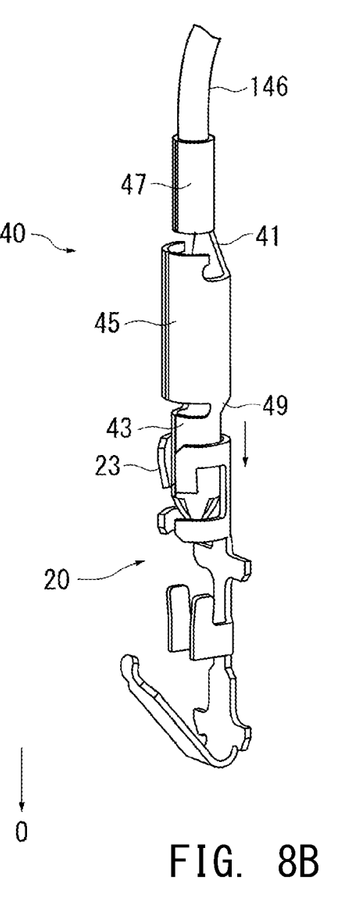

FIG. 1 is an overall cross-sectional view of a gas sensor (NOx sensor) 1 according to a first embodiment of the present invention, the cross section being taken in the direction of an axial line O, and FIG. 2 is a perspective view of a sensor element 10. FIGS. 3A and 3B are perspective views showing forward metal terminal members 20 and 30 held in a forward separator 90, and FIG. 4 is a cross-sectional view showing the forward metal terminal members 20 and 30 held in the forward separator 90. FIG. 5 is a perspective view of a rear metal terminal member 40, and FIG. 6 is a perspective view showing rear metal terminal members 40 held in a rear separator 95. FIG. 7 is a cross-sectional view taken along line A-A in FIG. 6, and FIGS. 8A and 8B are perspective views showing a rear metal terminal member 40 connected to a forward metal terminal member 20.

The gas sensor 1 is an NOx sensor for detecting the concentration of oxygen in exhaust gas from automobiles and various internal combustion engines.

In FIG. 1, the gas sensor 1 includes: a tubular metallic shell 138 having a threaded portion 139 formed on its outer surface and adapted for fixation to an exhaust pipe; a plate-shaped sensor element 10 extending in the direction of the axial line O (the longitudinal direction of the gas sensor 1, or the vertical direction in the drawing); a tubular ceramic sleeve 106 disposed so as to surround the circumference of the sensor element 10; a tubular forward separator 90 made of ceramic and disposed so as to surround the circumference of a rear end portion of the sensor element 10 inserted into a forward internal space of the forward separator 90; six forward metal terminal members 20 and 30 (only two forward metal terminal members 20 are illustrated in FIG. 1) inserted into and held in insertion holes 90h (90h1 and 90h2) extending through the forward separator 90 in the direction of the axial line O; a tubular rear separator 95 made of ceramic; and six rear metal terminal members 40 (only two of them illustrated in FIG. 1) held in the rear separator 95.

The rear separator 95 is disposed rearward of the forward separator 90 so as to be in contact therewith.

The forward separator 90 and the rear separator 95 correspond to the "separator" in the claims, and the rear metal terminal members 40 correspond to the "metal terminal" in the claims.

As shown in FIG. 4, the insertion holes 90h1 and 90h2 of the forward separator 90 are in communication with the internal space described above on the forward end side of the forward separator 90, and the forward metal terminal members 20 and 30 held in the insertion holes 90h1 and 90h2 face outer surfaces of a rear end portion of the sensor element 10 and are electrically connected to respective electrode pads (electrode portions) 11a formed on the outer surfaces.

As shown in FIG. 2, three electrode pads 11a are disposed on each of the opposite sides of the rear end portion of the sensor element 10 and arranged in its width direction. Specifically, one electrode pad 11a is disposed at the widthwise center of the rear end portion of the sensor element 10, and two electrode pads 11a are disposed forward of the one electrode pad 11a so as to be spaced apart from each other in the width direction.

The electrode pads 11a may be formed of, for example, a sintered body composed mainly of Pt.

A gas detection portion 11 at the forward end of the sensor element 10 is covered with a porous protection layer 14 made of, for example, alumina.

The metallic shell 138 is a generally tubular member formed of stainless steel and having a through hole 154 extending therethrough in the direction of the axial line and a ledge portion 152 protruding toward a radially inward region of the through hole 154. The sensor element 10 is disposed in the through hole 154 such that its forward end portion protrudes from the forward end of the through hole 154. The ledge portion 152 has an inward tapered surface inclined with respect to a plane perpendicular to the direction of the axial line.

Within the through hole 154 of the metallic shell 138, a generally annular ceramic holder 151 made of alumina, a powder filler layer 153 (hereinafter may be referred to as a talc ring 153), and the above-described ceramic sleeve 106 are stacked in this order from the forward end side to the rear end side so as to surround the circumference of the sensor element 10.

A crimp packing 157 is disposed between the ceramic sleeve 106 and a rear end portion 140 of the metallic shell 138. The rear end portion 140 of the metallic shell 138 is crimped so as to press the ceramic sleeve 106 forward through the crimp packing 157.

As shown in FIG. 1, a dual protector made of metal (e.g., stainless steel) is attached by, for example, welding to the outer circumference of a forward end portion (a lower portion in FIG. 1) of the metallic shell 138 and covers a protruding portion of the sensor element 10. The dual protector has a plurality of holes and is composed of an outer protector 142 and an inner protector 143.

A sleeve 144 is fixed to the outer circumference of a rear end portion of the metallic shell 138. Lead wires 146 are connected to rear end portions of the respective rear metal terminal members 40 and extend rearward from the rear end of the rear separator 95.

A grommet 170 made of rubber is disposed in a rear end (an upper end in FIG. 1) opening portion of the sleeve 144 and has lead wire insertion holes 170h into which six lead wires 146 (only two of them illustrated in FIG. 1) extending from the rear separator 95 are inserted.

The grommet 170 corresponds to the "elastic member" in the claims.

The forward separator 90 is disposed around a rear end portion (an upper end portion in FIG. 1) of the sensor element 10 protruding from the rear end portion 140 of the metallic shell 138 and has a collar portion 90p protruding radially outward from the outer surface of the forward separator 90. The collar portion 90p abuts against the sleeve 144 through a holding member 169, and the forward separator 90 is thereby held within the sleeve 144.

The rear separator 95 is disposed between the grommet 170 and the forward separator 90, and elastic force of the grommet 170 causes the rear separator 95 to press forward the forward separator 90. As a result, the collar portion 90p is pressed against the holding member 169, and the forward separator 90 and the rear separator 95 are thereby held within the sleeve 144 in a mutually connected condition (i.e., without separation in the direction of the axial line O).

FIGS. 3A and 3B are perspective views showing the forward metal terminal members 20 and 30 held in the forward separator 90. The lower side in FIGS. 3A and 3B corresponds to a forward end F. In the present embodiment, a total of six forward metal terminal members of two types, i.e., the forward metal terminal members 20 and 30, are used.

As shown in FIG. 4, the shapes of adjacent ones of the four forward metal terminal members 30 within the forward separator 90 are line-symmetric, and the two forward metal terminal members 20 facing each other within the forward separator 90 are line-symmetric.

Each forward metal terminal member 20 as a whole extends in the direction of the axial line O and includes a connection portion 23 to be connected to a corresponding rear metal terminal member 40, a generally plate-shaped body portion 21 connected to the forward end of the connection portion 23, and an elastic portion 22 bent toward the sensor element 10 at the forward end of the body portion 21.

The connection portion 23 has a cylindrical shape and a C-shaped cross section, and a forward end portion 43 of the rear metal terminal member 40 that has a cylindrical shape and a C-shaped cross section (see FIG. 5) is to be inserted into and connected to the tubular connection portion 23. In this case, the forward metal terminal member 20 is indirectly connected to a corresponding lead wire 146 through the rear metal terminal member 40.

The elastic portion 22 is bent rearward toward the sensor element 10 at the forward end of the body portion 21 and is to be elastically connected to one of the electrode pads 11a on the rear end side in FIG. 2. The elastic portion 22 can elastically deform radially with respect to the body portion 21.

The body portion 21 has holding portions 29 having different shapes and to be engaged with an inner wall, etc. of the forward separator 90.

Each forward metal terminal member 30 as a whole extends in the direction of the axial line O and integrally includes: a connection portion 33 to be connected to a corresponding rear metal terminal member 40; a generally plate-shaped body portion 31 connected to the forward end of the connection portion 33; and an elastic portion 32 bent toward the sensor element 10 at the forward end of the body portion 31.

The connection portion 33 has a cylindrical shape similar to the shape of the connection portion 23, and the forward end portion 43 of the rear metal terminal member 40 is to be inserted into and connected to the cylindrical connection portion 33, as in the case of the connection portion 23.

The elastic portion 32 is bent rearward toward the sensor element 10 at the forward end of the body portion 31 and is to be elastically connected to a corresponding one of the four electrode pads 11a located on the forward end side in FIG. 2. The elastic portion 32 can elastically bend radially from the body portion 31.

The body portion 31 has an L-shaped cross section and has holding portions having different shapes and to be engaged with an inner wall, etc. of the forward separator 90.

Each of the forward metal terminal members 20 and 30 can be produced by, for example, punching a blank from a single metal sheet (e.g., an Inconel (registered trade mark) sheet) and bending the punched blank into a prescribed shape, but this is not a limitation.

As shown in FIG. 4, the forward separator 90 has the insertion holes 90h1 and 90h2. The insertion holes 90h2 are disposed at four corners of the forward separator 90, and each of the insertion holes 90h1 is located between two insertion holes 90h2 arranged in the width direction of the sensor element 10.

The forward metal terminal members 20 and 30 are inserted into the insertion holes 90h1 and 90h2, respectively, and held in the forward separator 90.

The connection portions 23 and 33 of the forward metal terminal members 20 and 30 held in the forward separator 90 protrude rearward from the forward separator 90 (FIG. 3B).

As shown in FIG. 5, each rear metal terminal member 40 as a whole extends in the direction of the axial line O and integrally includes, sequentially from the rear end side: a lead wire connection portion 47 connected to a corresponding lead wire 146; a cylindrical central portion 45 having a C-shaped cross section; and a cylindrical forward end portion 43 having a C-shaped cross section. The forward end portion 43 and the central portion 45 are connected integrally through a forward neck portion 49, and the central portion 45 and the lead wire connection portion 47 are connected integrally through a rear neck portion 41.

The rear neck portion 41 corresponds the "neck portion" in the claims.

The rear metal terminal member 40 can be produced, for example, by punching a blank from a single metal sheet (e.g., SUS304) and bending the punched blank into a prescribed shape, but this is not a limitation.

The lead wire connection portion 47 has a cylindrical shape (a barrel shape formed by crimping). An exposed core of a forward end portion of the lead wire 146 with its coating removed is inserted into the lead wire connection portion 47, and the lead wire connection portion 47 is crimped to thereby hold the core externally.

The forward end portion 43 has a cylindrical shape and a tapered forward end. The forward end portion 43 of each rear metal terminal member 40 is fitted into a tubular connection portion 23 or 33, and the rear metal terminal member 40 is thereby electrically connected to a corresponding one of the forward metal terminal members 20 and 30.

The central portion 45 is larger in diameter than the lead wire connection portion 47 and the forward end portion 43, and a rearward-facing rearmost surface 45e of the central portion 45 (its rearward-facing surface located at the rearmost end) is located radially outward of the lead wire connection portion 47.

The rear neck portion 41 has an arc-shaped cross section, extends toward the rear end side with a radially inward inclination. The area of a cross section of the rear neck portion 41 that is orthogonal to the direction of the axial line O is smaller than those of the central portion 45 and the lead wire connection portion 47.

The rear neck portion 41 has different cross-sectional areas at different positions in the direction of the axial line O, and the cross-sectional area S1 of the rear neck portion 41 is its largest cross-sectional area (in this example, at a first connection portion J1 (which will be described later) connected to the central portion 45).

The cross-sectional area S2 of the central portion 45 and the cross-sectional area S3 of the lead wire connection portion 47 are the areas of the largest (generally annular) cross sections of the central portion 45 and the lead wire connection portion 47, respectively.

Ideally, the axial line of the rear separator 95 coincides with the axial line of the sensor element 10. However, these axial lines may be positionally offset from each other. Therefore, when the cross-sectional areas S1 to S3 are computed, the axial line of the rear separator 95 is used as the axial line O. Specifically, the axial line O of the rear separator 95 in a state in which the rear metal terminal member 40 is held in the rear separator 95 is used as a reference axial line for determining the cross-sectional areas.

A portion whose cross-sectional area S1 is 70% or less of a smaller one of the cross-sectional areas S2 and S3 is defined as the rear neck portion 41.

As described above, the cross-sectional area S1 of the rear neck portion 41 is smaller than the cross-sectional area S2 of the central portion 45 and the cross-sectional area S3 of the lead wire connection portion 47. When the rear metal terminal member 40 wobbles in the radial direction, stress is concentrated near the rear neck portion 41. Therefore, specifying circumferential lengths C1 and C2 described later is effective.

As shown in FIG. 6, the rear separator 95 has six insertion holes 95h arranged circumferentially. As shown in FIG. 7, each insertion hole 95h is larger in diameter on the forward end F side and is reduced in diameter stepwise in the vicinity of the center with respect to the direction of the axial line O, and the step has a forward-facing surface 95s.

The rear separator 95 has two protrusions 95p protruding forward from the peripheral edge portion of the forward-facing surface of the rear separator 95.

Each lead wire 146 is inserted in advance into a corresponding insertion hole 95h so as to protrude forward therefrom, and the lead wire connection portion 47 of a corresponding rear metal terminal member 40 is crimped and connected to the protruding portion of the lead wire 146 protruding forward from the rear separator 95. Next, part of the rear metal terminal member 40 on the lead wire 146 side is inserted into the insertion hole 95h from the forward end F side, and the lead wire 146 is pulled rearward. The rearward-facing rearmost surface 45e (see FIG. 5) of the central portion 45 of the rear metal terminal member 40 thereby abuts against the forward-facing surface 95s and is placed in position, and the rear metal terminal member 40 is held in the rear separator 95. Among the forward end portion 43, the central portion 45, and the lead wire connection portion 47 of the rear metal terminal member 40, the central portion 45 has the largest diameter.

As shown in FIG. 6, the forward end portion 43 of each rear metal terminal member 40 protrudes from the forward-facing surface of the rear separator 95.

The forward separator 90 shown in FIG. 3 and the rear separator 95 shown in FIG. 6 are disposed on the forward and rear sides, respectively, so as to be in contact with each other through the protrusions 95p. In this manner, as shown in FIGS. 8A and 8B, the forward end portion 43 of each rear metal terminal member 40 is fitted into and connected to the connection portion 23 of a corresponding forward metal terminal member 20.

The protrusions 95p support, in the direction of the axial line O, the forward metal terminal members 20 protruding from the rearward-facing surface of the forward separator 90 and the rear metal terminal members 40 protruding from the forward-facing surface of the rear separator 95 such that these terminals are not crushed between the forward separator 90 and the rear separator 95.

Although not illustrated, the forward metal terminal members 30 are also connected to corresponding rear metal terminal members 40 in the same manner. Specifically, the forward end portions 43 of the corresponding rear metal terminal members 40 are fitted into and connected to the connection portions 33 of the forward metal terminal members 30.

Namely, in the present embodiment, the rear metal terminal members 40 are electrically connected indirectly to the electrode pads 11a of the sensor element 10 through the respective forward metal terminal members 20 and 30.

Figure 9:
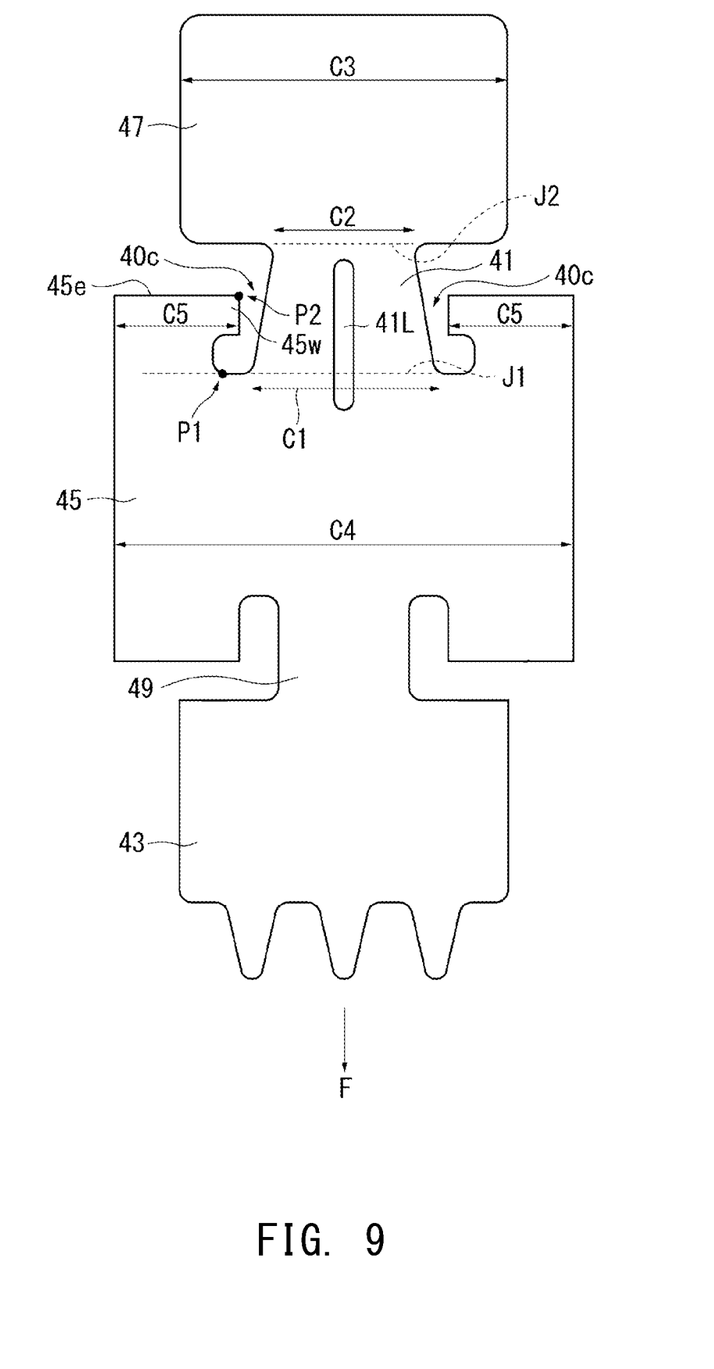
FIG. 9 is a development of the rear metal terminal member.
Figure 10:
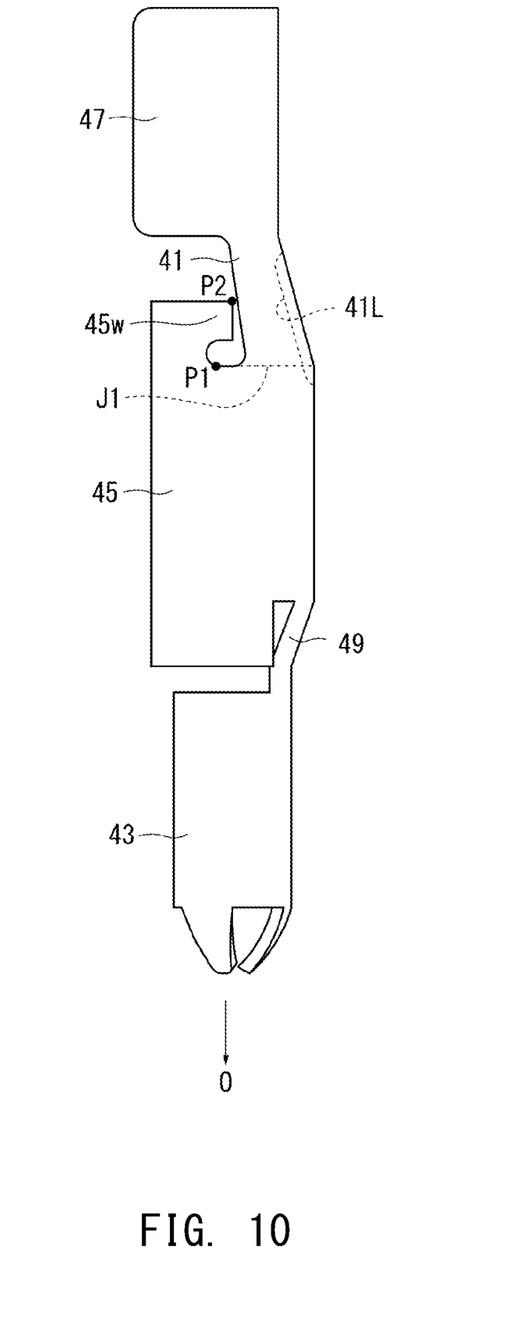
FIG. 10 is a side view of the rear metal terminal member.

Referring next to FIGS. 9 and 10, each rear metal terminal member 40, which is the feature of the present invention, will be described.

FIG. 9 is a development of the rear metal terminal member 40, i.e., shows an unbent plate-shaped member, and FIG. 10 is a side view of the rear metal terminal member 40.

As shown in FIG. 9, the circumferential length C1 of the first connection portion J1 between the central portion 45 and the rear neck portion 41 is longer than the circumferential length C2 of a second connection portion J2 between the lead wire connection portion 47 and the rear neck portion 41. This is because of the following reason.

As shown in FIG. 7, the rear neck portions 41 are inclined with respect to the direction of the axial line O, and the lead wire connection portions 47 and the central portions 45 are spaced apart from inner walls of the insertion holes 95h.

Therefore, when the gas sensor 1 vibrates during, for example, travel of the vehicle, the lead wire connection portions 47 and the central portions 45 wobble in the radial direction T. The rearward-facing rearmost surfaces 45e of the central portions 45 are engaged with inner walls of the insertion holes 95h of the rear separator 95 and are held in the insertion holes 95h, and therefore the central portions 45 wobble only slightly in the direction of the axial line O. This is also the case when the lead wire connection portions 47 protrude rearward from the rear separator 95.

Each of the forward end portions 43 is fitted into and held by the connection portion 23 or 33 of a corresponding forward metal terminal member 20 or 33, and the forward metal terminal members 20 and 33 are held in the forward separator 90. Therefore, the forward end portions 43 are indirectly held by the forward separator 90. The forward separator 90 and the rear separator 95 are in contact with each other through the protrusions 95p. The lead wires 146 extending rearward from the lead wire connection portions 47 are held by the grommet 170.

Therefore, the forward end portions 43 and the lead wires 146 wobble less in the radial direction as compared with the lead wire connection portions 47 (particularly their forward end portions) and the central portions 45.

In this case, stress concentrates on the rear neck portions 41 between the lead wire connection portions 47 and the central portions 45 which wobble greatly. In particular, the stress concentrates on the first connection portions J1 near the central portions 45, and the first connection portions J1 are likely to break or bend.

Therefore, each first connection portion J1 is formed such that the circumferential length C1 of the first connection portion J1 is larger than the circumferential length C2. The strength of the first connection portion J1 is thereby improved. Since the first connection portion J1 and the second connection portion J2 share the stress, breakage of the first connection portion J1 can be prevented.

In general, the first connection portion J1 and the second connection portion J2 are regions where the width of the rear metal terminal member 40 increases sharply (i.e., the rear metal terminal member 40 expands greatly in the circumferential direction approximately horizontally) from the rear neck portion 41, whereby the central portion 45 and the lead wire connection portion 47 are formed. However, in the case where the width of the rear metal terminal member 40 increases smoothly from the rear neck portion 41 toward the lead wire connection portion 47 so that a tapered portion is formed between the rear neck portion 41 and the lead wire connection portion 47, the second connection portion J2 is defined as a region of the tapered portion at which its cross-sectional area S1 is 70% of the cross-sectional area S3 as described above.

If the rear neck portion 41 has a cutout or a recess at which the cross section of the rear neck portion 41 orthogonal to the axial line is smaller in area than the cross section of the second connection portion J2, stress concentrates on this portion. Therefore, the rear neck portion 41 does not have a portion having a cross sectional area smaller than the cross sectional area of the second connection portion J2. Specifically, at the second connection portion J2, the cross-sectional area of the rear neck portion 41 is smallest.

When the degree of stress concentration at the first connection portion J1 is reduced in the manner described above, stress is applied also to the second connection portion J2. When the circumferential length C2 of the second connection portion J2 is 30 to 50% of the maximum circumferential length C3 of the lead wire connection portion 47, the strength of the second connection portion J2 is improved, and breakage of the second connection portion J2 can be prevented.

If the circumferential length C2 is less than 30% of the maximum circumferential length C3, the strength of the second connection portion J2 may not be improved sufficiently. If the circumferential length C2 exceeds 50% of the maximum circumferential length C3, the following occurs. When the lead wire connection portion 47 is crimped to reduce its diameter, the second connection portion J2 deforms together with the lead wire connection portion 47, and this may cause cracking of the second connection portion J2. Moreover, since the relation C1>C2 holds, the circumferential length C1 must be further increased. In this case, the total circumferential length C5 of the rearward-facing rearmost surface 45e decreases, and the rearward-facing rearmost surface 45e may not be easily engaged with the rear separator 95.

In the present embodiment, C1>C2 holds. The maximum circumferential length C4 of the central portion 45, the circumferential length C1, and the total circumferential length C5 of the rearward-facing rearmost surface 45e satisfy the relation C4≅C1+C5, so that there is a trade-off between C1 and C5. Specifically, when the circumferential length C1 is increased, the total circumferential length C5 is reduced accordingly, so that the rearward-facing rearmost surface 45e may not be easily engaged with the forward-facing surface 95s of the rear separator 95.

When a contact point P1 and a contact point P2 are defined as shown in FIG. 9, both C1 and C5 can be increased, and the rear metal terminal member 40 can be reliably held in the rear separator 95.

The contact point P1 and the contact point P2 are defined as follows.

In the case where the first connection portion J1 is located on the forward end F side of the rearward-facing rearmost surface 45e and a vertical line J1 is drawn to pass through the opposite ends of the first connection portion J1 in the circumferential direction (in FIG. 9, the virtual line J1 is the same as a broken line representing the first connection portion J1), two cutouts 40c are formed on opposite sides of the rear neck portion 41; i.e., formed between the central portion 45 and the opposite ends of the first connection portion J1, such that the cutouts 40c extend forward from the rearward-facing rearmost surface 45e and reach the virtual line J1.

At least one of the cutouts 40c is formed such that its contour is in contact with the virtual line J1 at a plurality of contact points and with the rearward-facing rearmost surface 45e at the contact point P2. The contact point P1 is one of the plurality of contact points that is farthest from the rear neck portion 41 in the circumferential direction. The contact point P2 is closer to the rear neck portion 41 than the contact point P1 in the circumferential direction.

Since the contour of the cutout 40c is closer to the rear neck portion 41 on the rear end side and the contact point P2 is closer to the rear neck portion 41 than the contact point P1, the total circumferential length C5 does not decrease even when the circumferential length C1 is increased, and both the lengths C1 and C5 can be increased. Therefore, the rear metal terminal member 40 can be reliably held in the rear separator 95.

When the total circumferential length C5 of the rearward-facing rearmost surface 45e is small, the contact length between the rearward-facing rearmost surface 45e and the forward-facing surface 95s of the rear separator 95 is small, and the force with which the rear metal terminal members 40 are held by the rear separator 95 may decrease.

Therefore, preferably, the total circumferential length C5 is 50% or more of the maximum circumferential length C4.

In the example in FIGS. 9 and 10, a portion of the central portion 45 near the contact point P2 is formed as a shoulder portion 45w having a prescribed width in the direction of the axial line O. In this case, the rearward-facing rearmost surface 45e has sufficient strength even near the contact point P2, and the rear metal terminal member 40 can be held in the rear separator 95 more reliably.

Figure 11:
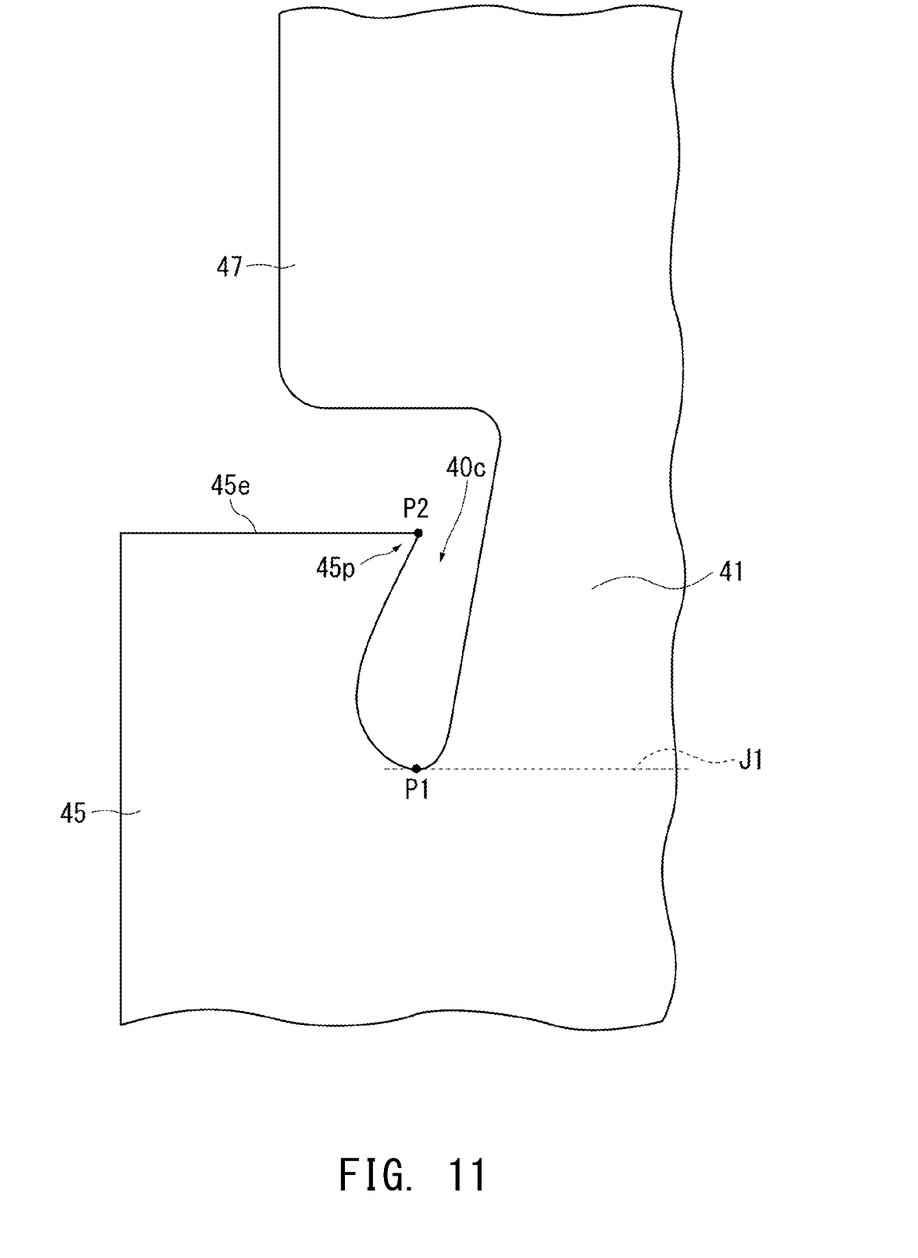
FIG. 11 is a development showing a modification of the rear metal terminal member.

In a modification shown in FIG. 11, a portion of the central portion 45 near the contact point P2 is formed as a protrusion 45p pointed toward the contact point P2. In this case, the portion of the central portion 45 near the contact point P2 does not have a sufficient width in the direction of the axial line O. Therefore, the strength of the rearward-facing rearmost surface 45e is low near the contact point P2, and the rearward-facing rearmost surface 45e may deform. Therefore, near the contact point P2, the rearward-facing rearmost surface 45e is not easily engaged with the forward-facing surface 95s of the rear separator 95, and the force with which the rear metal terminal members 40 are held by the rear separator 95 may be lower than that in the example in FIG. 9. However, the example in FIG. 11 is not excluded from the present invention.

In the example in FIG. 11, the contour of a cutout 40c extending toward the virtual line J1 has an arc-shaped forward end, and the contour of the cutout 40c is in contact with the virtual line J1 at one point only. Therefore, this contact point is used as the contact point P1.

In fact, the rear neck portion 41 is narrower and has lower strength than the central portion 45 and the lead wire connection portion 47. Therefore, when a rib 41L extending in the direction of the axial line O is provided on the rear neck portion 41 as shown in FIGS. 9 and 10, the strength of the rear neck portion 41 is improved, and breakage of the rear metal terminal member 40 can be further prevented.

The rib 41L is formed so as to straddle at least the first connection portion J1. In this manner, the strength of the first connection portion J1 on which stress concentrates can be further improved.

It is preferable that the rib 41L is formed by recessing the rear neck portion 41 radially inward such that the rib 41L does not protrude outward as shown in FIG. 10. In this case, the rib 41L does not interfere with the wall surface of the insertion hole 95h of the rear separator 95. The phrase "radially inward" means a direction from the rib 41L toward the axial center of the central portion 45 of the rear metal terminal member 40.

It will be appreciated that the present invention is not limited to the embodiments described above and encompasses various modifications and equivalents within the spirit and scope of the present invention.

The shapes etc. of the metal terminals and the separators are not limited to those in the above embodiments. The separator may not be composed of two parts, i.e., the forward separator and the rear separator, and may be composed of a single part.

Each metal terminal may not be cylindrical and may be a tube having a prism shape such as a quadrangular prism shape. The metal terminal may not be a fully closed tube and may be at least part of a tube (e.g., a C-shaped tube).

Examples of the gas sensor include, in addition to the NOx sensor, an oxygen sensor and a full range gas sensor.

DESCRIPTION OF REFERENCE NUMERALS

1: gas sensor
10: sensor element

11a: electrode portion (electrode pad)
40: metal terminal (rear metal terminal member)
40c: cutout
41: neck portion (rear neck portion)
41L: rib
43: forward end portion
45: central portion
45e: rearward-facing rearmost surface of central portion
47: lead wire connection portion
90: separator (forward separator)
95: separator (rear separator)
95s: forward-facing surface of separator
146: lead wire
170: elastic member (grommet)
O: axial line
S1: area of cross section of neck portion that is orthogonal to direction of axial line
S2: area of cross section of central portion that is orthogonal to direction of axial line
S3: area of cross section of lead wire connection portion that is orthogonal to direction of axial line
J1: first connection portion (virtual line)
J2: second connection portion

The invention claimed is:

1. A gas sensor comprising:
   a sensor element extending in a direction of an axial line of the gas sensor, the sensor element having an electrode portion on a surface of a rear end portion thereof;
   a metal terminal extending in the direction of the axial line and electrically connected to the electrode portion;
   a separator that holds the metal terminal and is disposed rearward of the sensor element;
   a lead wire connected to a rear end portion of the metal terminal and extending rearward from the separator; and
   an elastic member that holds the lead wire extending rearward from the separator,
   wherein the metal terminal includes a forward end portion electrically connected to the electrode portion, a central portion, and a lead wire connection portion connected to the lead wire,
   wherein the forward end portion, the central portion, and the lead wire connection portion are integrally formed and arranged in this order from a forward side of the metal terminal,
   wherein the forward end portion or the central portion is held by the separator,
   wherein the central portion and the lead wire connection portion are integrally connected to each other through a neck portion whose cross sectional area orthogonal to the direction of the axial line is smaller than a cross sectional area of the central portion or a cross sectional area of the lead wire connection portion,
   wherein a rearward-facing rearmost surface of the central portion is engaged with a forward-facing surface of the separator,
   wherein a circumferential length of a first connection portion provided between the central portion and the neck portion is longer than a circumferential length of a second connection portion provided between the lead wire connection portion and the neck portion, and
   wherein the neck portion inclines inwardly toward a rear end side thereof in a radial direction.

2. The gas sensor according to claim 1,
   wherein the first connection portion is located forward with respect to the rearward-facing rearmost surface,
   wherein two cutouts are respectively formed between the central portion and opposite ends of the first connection portion in a circumferential direction, the cutouts extending forward from the rearward-facing rearmost surface and reaching a virtual line passing through the opposite ends of the first connection portion,
   wherein at least one of the cutouts is formed such that its contour is in contact with the virtual line at a plurality of contact points, including a first contact point that is farthest from the neck portion in the circumferential direction, and with the rearward-facing rearmost surface at a second contact point, which is closer to the neck portion than the first contact point in the circumferential direction.

3. The gas sensor according to claim 1, wherein the neck portion has a rib that extends in the direction of the axial line so as to straddle at least the first connection portion.

4. The gas sensor according to claim 3, wherein the rib inwardly recesses in a radial direction of the neck portion.

* * * * *